(12) United States Patent
Page et al.

(10) Patent No.: US 7,135,554 B1
(45) Date of Patent: Nov. 14, 2006

(54) METHOD OF FORMING A POLYMERIZED HEMOGLOBIN SOLUTION FROM STABILIZED HEMOGLOBIN

(75) Inventors: Thomas C. Page, Watertown, MA (US); Jose O. Torres, Norton, MA (US); William R. Light, Natick, MA (US)

(73) Assignee: Biopure Corporation, Cambridge, MA (US)

( * ) Notice: Subject to any disclaimer, the term of this patent is extended or adjusted under 35 U.S.C. 154(b) by 0 days.

(21) Appl. No.: 10/998,861

(22) Filed: Nov. 29, 2004

Related U.S. Application Data

(63) Continuation of application No. 10/765,570, filed on Jan. 27, 2004, now abandoned.

(51) Int. Cl.
*C07K 14/805* (2006.01)

(52) U.S. Cl. .............. 530/385; 530/402; 514/6

(58) Field of Classification Search .............. 530/380, 530/385
See application file for complete search history.

(56) References Cited

U.S. PATENT DOCUMENTS

| | | | |
|---|---|---|---|
| 3,577,522 A * | 5/1971 | Hymes | .............. 424/78.38 |
| 3,925,344 A | 12/1975 | Mazur | |
| 4,001,200 A | 1/1977 | Bonsen et al. | |
| 4,001,401 A | 1/1977 | Bonsen et al. | |
| 4,061,736 A | 12/1977 | Morris et al. | |
| 4,376,059 A | 3/1983 | Davis et al. | |
| 4,473,496 A | 9/1984 | Scannon | |
| 4,529,719 A | 7/1985 | Tye | |
| 4,584,130 A | 4/1986 | Bucci et al. | |
| 4,598,064 A | 7/1986 | Walder | |
| 4,600,531 A | 7/1986 | Walder | |
| 4,670,417 A | 6/1987 | Iwasaki et al. | |
| 4,738,952 A | 4/1988 | Ecanow et al. | |
| 4,826,811 A | 5/1989 | Sehgal et al. | |
| 4,900,780 A | 2/1990 | Cerny | |
| 5,084,558 A | 1/1992 | Rausch et al. | |
| 5,128,452 A | 7/1992 | Hai et al. | |
| RE34,271 E | 6/1993 | Walder | |
| 5,250,665 A | 10/1993 | Kluger et al. | |
| 5,362,855 A | 11/1994 | Garlick et al. | |
| 5,464,814 A | 11/1995 | Sehgal et al. | |
| 5,532,352 A | 7/1996 | Pliura et al. | |
| 5,753,616 A | 5/1998 | Rausch et al. | |
| 5,840,852 A | 11/1998 | Rausch et al. | |
| 5,895,810 A * | 4/1999 | Light et al. | .............. 530/385 |
| 6,271,351 B1 | 8/2001 | Gawryl et al. | |
| 6,552,173 B1 | 4/2003 | Sehgal et al. | |

OTHER PUBLICATIONS

Tye, et al., "Modification of Hemoglobin—Tetrameric Stabilization," *Advances in Blood Substitute Research*, p. 41-49 (1989).

Ritter, S. K., "Passing a Blood Test," *C & EN*, p. 37-44, May 18, 1998.

Feola, et al., "Toxicity of Polymerized Hemoglobin Solutions," *Surgery, Gynecology & Obstetrics*, 166:211-222, Mar. 1988.

* cited by examiner

*Primary Examiner*—Jon Weber
*Assistant Examiner*—Anand Desai
(74) *Attorney, Agent, or Firm*—Hamilton, Brook, Smith & Reynolds, P.C.

(57) ABSTRACT

A stabilized hemoglobin solution is contacted with polymerizing agent. The stabilized hemoglobin solution includes stabilized tetrameric hemoglobin. At least a portion of the stabilized tetrameric hemoglobin is polymerized by reaction with the polymerizing agent, thereby producing a polymerized hemoglobin solution. In one embodiment, the stabilized hemoglobin solution includes a filtrate formed by filtrating polymerized solution of native hemoglobin through a filter having a molecular weight cut off of about 100 kD.

41 Claims, 2 Drawing Sheets

METHOD OF FORMING A POLYMERIZED HEMOGLOBIN SOLUTION FROM STABILIZED HEMOGLOBIN

RELATED APPLICATION

This application is a continuation of U.S. application Ser. No. 10/765,570, filed Jan. 27, 2004 now abandoned. The entire teachings of the above application are incorporated herein by reference.

BACKGROUND OF THE INVENTION

In its natural form, mammalian hemoglobin is tetrameric having a molecular weight of approximately 65 kD. Hemoglobin is structurally comprised of two alpha and two beta subunits with the alpha/beta subunits forming pairs. Each subunit contains a heme group and a polypeptide chain, called globin. In mammals, hemoglobin is encapsulated in erythrocytes (red blood cells), by a cell membrane which consists of proteins, phospholipids and cholesterol. See *Clinical Hematology*, by Wintrobe, 6th ed., pages 138–199, (1967).

Hemoglobin exists in equilibrium between the tetrameric and dimeric (approximately 32 kD) forms (Bunn, H. F. et al., *Transperiod Assn. Am. Physicians,* 81:187, (1968)). Equilibrium is influenced by concentration, oxygenation state, and temperature. When present extracelluarly, the dimers and tetramers are excreted by the kidney and are rapidly (half-life time 2 to 4 hours) removed from the circulatory system. Stabilized tetramers have a half-life of about 6 to 15 hours, while polymers remain in the blood stream longer. Typically, solutions comprising non-cross-linked hemoglobin have a circulating half life of 2–4 hrs when administered to an animal. Furthermore, unstabilized and even cross-linked tetrameric hemoglobin can be harmful to humans due to toxicity to the kidneys. Accordingly, polymers are the preferred form. To increase the half-life of hemoglobin in blood circulation and to reduce potential harmful effects of lower molecular weight forms of hemoglobin, native hemoglobin has been cross linked using a cross-linking agent to produce a stabilized form, so that dimer levels are significantly reduced. Polymers of hemoglobin with molecular weight greater than about 65 kD have been formed using polymerizing agents. In some cases, the cross-linking and the polymerizing agent are the same.

For use in humans, blood-substitutes comprising hemoglobin generally should include no more than 10% unstabilized hemoglobin. Unfortunately, polymerization of native hemoglobin by cross-linking can result in a solution wherein 50% or more of the hemoglobin is unstabilized or stabilized tetrameric hemoglobin, which generally is an unacceptably high level of these forms of hemoglobin. Therefore, a blood-substitute suitable for human use generally requires the removal of at least a portion of unstabilized or stabilized tetrameric hemoglobin to acceptable levels, resulting in significant waste of the starting material and high production costs.

For example, hemoglobin polymerized by exposure to a polymerizing agent is typically passed through a 100 kD molecular weight filter to remove the lower molecular weight hemoglobin from hemoglobin polymers. The lower molecular weight hemoglobin passes through the filter and into the filtrate. The filtrate is discarded as waste, typically resulting in a loss of up to about 50% of the isolated hemoglobin.

Therefore, a need exists to improve the efficiency of the hemoglobin polymerization process to improve the yield of polymerized hemoglobin blood-substitute from isolated hemoglobin.

SUMMARY OF THE INVENTION

The present invention is directed to a method for forming a polymerized hemoglobin solution. According to the method of the present invention, a stabilized hemoglobin solution is contacted with a polymerizing agent. The stabilized hemoglobin solution includes cross-linked tetrameric hemoglobin. At least a portion of the tertrameric hemoglobin is further polymerized, thereby forming the polymerized hemoglobin solution of the present invention.

In one embodiment, the method for polymerizing hemoglobin includes contacting a stabilized hemoglobin solution with glutaraldehyde solution, wherein about 10 grams of glutaraldehyde are added per kilogram of hemoglobin in the stabilized hemoglobin solution. The stabilized hemoglobin solution includes a physiological buffer and stabilized hemoglobin. At least a portion of the stabilized hemoglobin is further polymerized, thereby forming the polymerized hemoglobin solution.

In another embodiment, the method for polymerizing hemoglobin includes contacting a stabilized hemoglobin solution with glutaraldehyde solution, wherein about 10 grams of glutaraldehyde are added per kilogram of hemoglobin in the stabilized hemoglobin solution. The stabilized hemoglobin solution comprises N-acetyl-L-cysteine (NAC) at a concentration of about 12 mM, sodium lactate at a concentration of about 27 mM, sodium chloride at a concentration of about 115 mM, potassium chloride at a concentration of about 4 mM, calcium chloride at a concentration of about 1.36 mM and having a pH of about 7.6 to about 7.9. The stabilized hemoglobin solution includes tetrameric hemoglobin. At least a portion of the tetrameric hemoglobin is further polymerized, thereby generating polymerized hemoglobin.

In another embodiment, the method for forming a polymerized hemoglobin solution comprises contacting a stabilized hemoglobin solution with glutaraldehyde wherein about 10 grams of glutaraldehyde are added per kilogram of hemoglobin present in the stabilized hemoglobin solution. The stabilized hemoglobin solution includes tetrameric and polymeric hemoglobin. The stabilized hemoglobin solution includes NAC at a concentration of about 12 mM, sodium lactate at a concentration of about 27 mM, sodium chloride at a concentration of about 115 mM, potassium chloride at a concentration of about 4 mM, calcium chloride at a concentration of about 1.36 mM and having a pH of about 7.6 to about 7.9. At least a portion of the hemoglobin solution is polymerized. The polymerized hemoglobin is directed through a filter having a molecular weight cut off of at least about 100 kD, and the retentate is obtained, forming a polymerized hemoglobin solution, wherein no more than about 15% by weight of the hemoglobin present in the retentate has an average molecular weight of about 500 kD or more, and no more than about 10% by weight of the hemoglobin present in the retentate has a molecular weight of about 65 kD or less.

The present invention results in a significant increase in the efficiency of producing a blood-substitute from isolated hemoglobin. Surprisingly, the hemoglobin of a stabilized hemoglobin solution can be further polymerized. This occurs even though the hemoglobin solution contains stabilized or cross-linked hemoglobin and even though the stabilized hemoglobin solution includes buffer and solute components that are different than that employed for polymerization of native hemoglobin. Therefore, glutaraldehyde-stabilized hemoglobin, for example, which would otherwise be discarded, can be polymerized. The present invention lowers the cost of producing a blood-substitute because it allows the recovery of tetrameric hemoglobin, which often constitutes as much as 50% of the total hemoglobin subjected to polymerization, to produce a polymerized hemoglobin blood-substitute with physiological and stability parameters similar to the polymerized hemoglobin produced from polymerization of native hemoglobin, and prior to being subjected to a process to remove tetrameric hemoglobin.

DETAILED DESCRIPTION OF THE INVENTION

Figure 1:
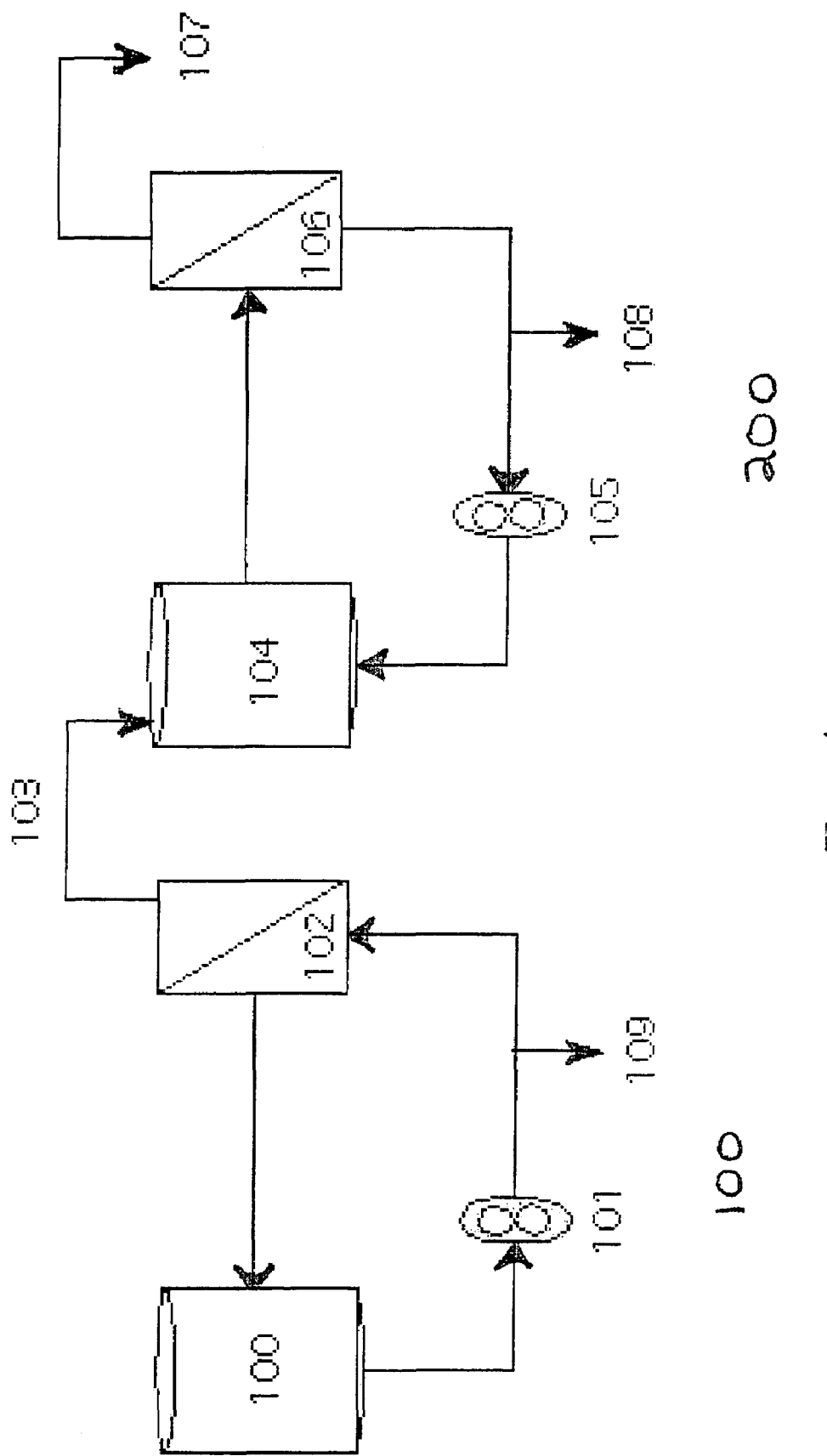
FIG. 1 is a schematic of the fractionation process and recovery of stabilized hemoglobin solution (HBOC-F).

The present invention is directed to a method for producing a blood-substitute using hemoglobin that previously has been exposed to cross-linking and/or polymerizing agents. Hemoglobin previously exposed to cross-linking agent is also referred to herein as "stabilized hemoglobin solution." Stabilized hemoglobin solution can include intra- and intermolecularly cross-linked hemoglobin. As used herein, intramolecularly cross-linked hemoglobin includes hemoglobin where all four subunits of a hemoglobin tetramer are covalently cross-linked to each other. Intramolecularly cross-linked hemoglobin can also include hemoglobin where two or three subunits of hemoglobin are covalently cross-linked to each other. Stabilized hemoglobin solution can also include more than four subunits of hemoglobin cross-linked together. Two or more tetramers covalently cross-linked together is also referred to herein as hemoglobin polymer. Stabilized hemoglobin solution can include hemoglobin tetramers and/or hemoglobin capable of dissociating into dimeric and monomeric subunits.

In one embodiment, stabilized hemoglobin solution includes stabilized hemoglobin that has undergone a chemical reaction between primary amino groups on the surface of the hemoglobin and glutaraldehyde. Stabilized hemoglobin solution can also be obtained as described, for example, in U.S. Pat. No. 6,610,832 B1, WO 01/34648 A1, U.S. Pat. No. 6,083,909, U.S. Pat. No. 5,770,727, and U.S. Pat. No. 6,552,173 B2; the teachings of which are incorporated herein in their entirety.

In one embodiment, the stabilized hemoglobin solution includes hemoglobin removed after polymerization of native hemoglobin, where the removed hemoglobin includes hemoglobin that has been exposed to polymerizing conditions and then passed into the filtrate of a 100 kD ultrafilter, as described in U.S. Pat. No. 6,610,832 B1, issued to Gawryl, et al. (the teachings of which are incorporated herein in their entirety). Stabilized hemoglobin solution, suitable for use in the present invention, can be generated from hemoglobin isolated from suitable sources, such as described in U.S. Pat. No. 6,610,832 B1.

In one embodiment, stabilized hemoglobin solution is obtained as described in U.S. Pat. No. 6,610,832 B1. Briefly, hemoglobin is isolated from a suitable source (also referred to herein as "freshly isolated" or "native" hemoglobin), deoxygenated, and transferred to a suitable buffer for polymerization. The native hemoglobin is then exposed to a polymerizing agent, generating a polymerized hemoglobin solution. The polymerized hemoglobin solution can then be stabilized by suitable means. After polymerization and stabilization of the deoxygenated, freshly isolated hemoglobin, the polymerized hemoglobin solution is transferred to a suitable storage buffer and subjected to a fractionation step, where lower molecular weight hemoglobin is removed from the polymerized hemoglobin solution by filtration through a 100 kD ultrafilter. The polymerized hemoglobin solution in a suitable storage buffer prior to fractionation is also referred to herein as "HBOC-301." The filtrate (HBOC-F, also referred to herein as stabilized hemoglobin solution), containing the lower molecular weight hemoglobin is typically discarded, and the retentate is packaged for use as a blood-substitute for humans (HBOC-201).

As described herein, the present invention includes exposing a stabilized hemoglobin solution (for example, HBOC-F, described above) to a polymerizing agent to further polymerize at least a portion of the hemoglobin present in the stabilized hemoglobin solution. Stabilized hemoglobin solution that has been further polymerized is also referred to herein as HBOC-302. It is understood that any hemoglobin present in the stabilized hemoglobin solution can also be polymerized or cross-linked.

Stabilized hemoglobin solution can be obtained by exposing a solution comprising native hemoglobin to an agent that can act as both cross-linking and polymerizing agent to polymerize the hemoglobin as is described above and in U.S. Pat. No. 5,955,581 and U.S. Pat. No. 6,610,832 B1. Examples of suitable agents include polyfunctional agents that will cross-link hemoglobin proteins, such as glutaraldehyde, succindialdehyde, activated forms of polyoxyethylene and dextran, α-hydroxy aldehydes, such as glycolaldehyde, N-maleimido-6-aminocaproyl-(2'-nitro,4'-sulfonic acid)-phenyl ester, m-maleimidobenzoic acid-N-hydroxysuccinimide ester, succinimidyl 4-(N-maleimidomethyl) cyclohexane-1-carboxylate, sulfosuccinimidyl-4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl (4-iodoacetyl)aminobenzoate, sulfosuccinimidyl(4-iodoacetyl)aminobenzoate, succinimidyl 4-(p-maleimidophenyl)butyrate, sulfosuccinimidyl 4-(p-maleimidophenyl)butyrate, 1-ethyl-3-(3-dimethylaminopropyl)carbodiimide hydrochloride, N,N'-phenylene dimaleimide, and compounds belonging to the bisimidate class, the acyl diazide class or the aryl dihalide class, among others.

In one embodiment, the stabilized hemoglobin solution includes a physiological buffer or physiological buffer components. In one embodiment, the stabilized hemoglobin solution includes at least about 115 mM chloride ion. This is in contrast to previously described methods of polymerizing native hemoglobin where the hemoglobin solution included chloride ion at a concentration of no more than about 35 mM.

In another embodiment, the stabilized hemoglobin solution includes one or more physiological electrolytes during exposure to the polymerizing agent. The stabilized hemoglobin solution can include, for example, one or more of the following electrolytes: NaCl at a concentration of about 570 to about 660 mg/100 ml (or about 98 to about 106 mM), KCl at a concentration of about 27 to 30 mg/100 ml (or about 3.6 to about 4.4 mM) and $CaCl_2 \cdot 2H_2O$ at a concentration of about 18 to 22 mg/100 ml (or about 1.2 to about 1.5 mM). In a more particular embodiment, the stabilized hemoglobin solution includes about 115 mM NaCl, about 4 mM KCl and about 1.36 mM $CaCl_2.2H_2O$. This is in contrast to previously described methods for polymerizing native hemoglobin which included tribasic sodium phosphate at 1.05 g/l and dibasic sodium phosphate at 2.8 g/l, in the absence of additional electrolytes.

The stabilized hemoglobin solution can include a reducing agent. The reducing agent is included as an oxygen scavenger to enhance the storage stability of the polymerized hemoglobin blood-substitute. During storage, in the absence of a reducing agent, many hemoglobin solutions oxidize from physiologically active form to the inactive form, methemoglobin. Reducing agents include suitable sulfhydryl containing compounds including non-toxic reducing agents, such as NAC, D- or L-cysteine, γ-glutamyl-cysteine, glutathione, 2,3-dimercapto-1-proponal, 1,4-butanedithiol, thioglycalate, and other biologically compatible sulfhydryl compounds. In one embodiment, the stabilized hemoglobin solution contains NAC at a concentration of about 0.13 to about 0.22 g/100 ml (or about 8 to about 13 mM). In a more particular embodiment, the stabilized hemoglobin solution contains NAC at a concentration of about 0.2 g/100 ml.

In addition, the stabilized hemoglobin solution can include other physiological components, for example, sodium lactate at a concentration of about 2.9 to about 3.3 g/l (or about 26 to about 29 mM). In a more particular embodiment, the stabilized hemoglobin solution includes sodium lactate at a concentration of 3.04 g/l.

In one embodiment, the stabilized hemoglobin solution includes N-acetyl-L-cysteine at a concentration of about 130 to about 220 mg/100 ml, sodium lactate at a concentration of about 290 to about 330 mg/100 ml, sodium chloride at a concentration of about 570 to about 620 mg/100 ml, potassium chloride at a concentration of about 27 to about 33 mg/100 ml, calcium chloride.$2H_2O$ at a concentration of about 18 to about 22 mg/100 ml and having a pH of about 7.6 to about 7.9, A suitable aqueous medium comprises "Lactated Ringer's Injection" as described in the USP-NF, U.S. Pharmacopeia, Inc., modified by the addition of 0.2% NAC.

In one embodiment, the stabilized hemoglobin solution comprises about 5 to about 10% of total hemoglobin in the form of dimers, about 40 to about 70% of total hemoglobin in the form of tetramers, about 20 to about 30% of total hemoglobin in the form of octamers, and no more than 1% of total hemoglobin in the form of high molecular weight (HMW, >500 kD) hemoglobin. In another embodiment, the stabilized hemoglobin solution comprises about 8% of total hemoglobin in the form of dimers, about 55% of total hemoglobin in the form of tetramers, about 26% of total hemoglobin in the form of octamers and less than 1% of total hemoglobin in the form of HMW hemoglobin. The remaining hemoglobin has a molecular weight of about 130 kD to about 500 kD. In addition, the stabilized hemoglobin solution comprises no more than 5% metHb.

To polymerize the hemoglobin of the stabilized hemoglobin solution, the stabilized hemoglobin solution is exposed to a polymerizing agent such as one or more agents described above. In one embodiment, the stabilized hemoglobin solution is exposed to glutaraldehyde at about 1 to about 20 grams of glutaraldehyde per kilogram of hemoglobin. In a more particular embodiment, a stabilized hemoglobin solution containing 4 g/dl of hemoglobin is exposed to about 10 grams of glutaraldehyde per kilogram of hemoglobin. In still another embodiment about 9.2 grams of glutaraldehyde are added per kilogram of hemoglobin in the stabilized hemoglobin solution. This is in contrast to the polymerization of freshly isolated hemoglobin (or native) as described above, where over 30 grams of glutaraldehyde are added per kilogram of hemoglobin.

As described herein, the stabilized hemoglobin solution is polymerized and diafiltered against a physiological buffer (described above), producing HBOC-302.

The hemoglobin of HBOC-302 meets the hemoglobin molecular weight distribution target of HBOC-301. In one embodiment, no greater than about 10% of the total hemoglobin in the polymerized hemoglobin solution formed by the method of the invention is comprised of HMW hemoglobin, about 45% to about 55% of total hemoglobin is in the form of a tetramers plus octamers, and about 30% to about 40% of total hemoglobin is low molecular weight hemoglobin, having a molecular weight of about 65 kD or less. In still another embodiment, the polymerized hemoglobin solution, formed by the method of the present invention, comprises no more than about 5% of total hemoglobin in the form of HMW hemoglobin, about 52% of total hemoglobin in the form of tetramers plus octamers, and about 32% of total hemoglobin in the form of low molecular weight hemoglobin. The remaining hemoglobin has a molecular weight of about 130 kD to about 500 kD. In addition, in one embodiment, the polymerized hemoglobin solution formed by the method of the present invention comprises less than about 10% of the total hemoglobin.

In another embodiment, to obtain a hemoglobin blood-substitute suitable for human use (HBOC-201), the polymerized hemoglobin formed by the method of the present invention can be diafiltered against physiological buffer to remove lower molecular weight hemoglobin species (e.g., hemoglobin having a molecular weight of about 65 kD or less). The presence of lower molecular weight hemoglobin species can be determined by gel permeation chromatography run under dissociating conditions. In one embodiment, HBOC-302 is diluted prior to diafiltration.

The diafiltration is conducted such that the hemoglobin solution retained by the filter meets the target molecular weight distribution for the human use blood substituted (HBOC-201). Specifically, in one embodiment, no more than about 15% by weight of the total hemoglobin present in the retentate is HMW hemoglobin, up to about 5% by weight of the total hemoglobin present in the retentate has a molecular weight of 65 kD or less, and up to about 22% of total hemoglobin present in the retentate comprises tetramers plus octamers. The remaining hemoglobin has a molecular weight of about 130 kD to about 500 kD.

The filtrate comprising the lower molecular weight hemoglobin obtained during diafiltration of HBOC-302 is also referred to herein as HBOC-F and can also be used in the method of the present invention.

As described herein, stabilized hemoglobin solution, such as HBOC-F, has been found to be a suitable substrate for further polymerization. Polymerized, stabilized hemoglobin solution (HBOC-302) or retentate is produced. Surprisingly, the polymerized, stabilized hemoglobin solutions of the present invention have substantially the same functional and stability properties as polymerized hemoglobin solutions produced from native hemoglobin. Furthermore, as demonstrated herein, stabilized hemoglobin solution, obtained for example as the filtrate of polymerized, native hemoglobin, surprisingly requires no adjustment to buffer or electrolyte conditions prior to exposure to the polymerizing agent.

Exemplification

The present invention will now be illustrated by the following examples that are not intended to be limiting in any way.

Example 1

Production of Stabilized Hemoglobin Solution (HBOC-F)

Stabilized hemoglobin solution was obtained as described in U.S. Pat. No. 6,610,832 B1, which describes the production of hemoglobin blood substitute. As described in U.S. Pat. No. 6,610,832 B1, bovine hemoglobin was obtained and polymerized to form polymerized Hb blood-substitute.

FIG. 1 shows fractionation loop 100 and concentration loop 200. The polymerized Hb blood-substitute was diluted to a concentration of 5.0 g/dl by adding filtered, deoxygenated low pH buffer (27 mM sodium lactate, 12 mM NAC, 115 mM NaCl, 4 mM KCl, and 1.36 mM $CaCl_2$ in water for injection (WFI), (pH 5.0)) to the polymerization reactor 101. The diluted blood substitute was then diafiltered in fractionation loop 100. Fractionation loop 100 comprises recirculation vessel 100, 100 kD fractionation filter 102, permeate line 103, port 109, and pump 101. The diluted blood substitute was recirculated over 102 against a filtered deoxygenated buffer containing 27 mM sodium lactate, 12 mM NAC, 115 mM NaCl, 4 mM KCl, and 1.36 mM $CaCl_2$ in WFI, (pH 7.8). As the low molecular weight hemoglobin was removed 103, the tank volume was reduced to maintain the hemoglobin concentration at about 5 g/dL.

Diafiltration was continued until the blood-substitute contained less than or equal to about 2.5% stabilized tetrameric and unstabilized tetrameric species by gel-permeation chromatography (GPC) when run under dissociating conditions (10.5 g/l BisTris, 152.6 g/l $MgCl_2$, 37 mg/l EDTA (pH 6.5)). Diafiltration was run under conditions of low transmembrane pressure with a restricted permeate line 103. The filtrate (HBOC-F) recovered at this stage was concentrated to 13 g/dL in concentration loop 200. Concentration loop 200 comprises recirculation vessel 104, 30 kD ultrafilter 106, permeate line 107, port 108, and pump 105. The retentate blood-substitute (HBOC-201) was passed through 106 until the concentration of the blood-substitute was about 130 g/l. The stable concentrated blood-substitute was then stored in a suitable container having a low oxygen environment and a low oxygen in-leakage. HBOC-F was used as the stabilized hemoglobin solution and subjected to further polymerization as described below.

Example 2

Large-Scale Polymerization of Stabilized Hemoglobin

Figure 2:
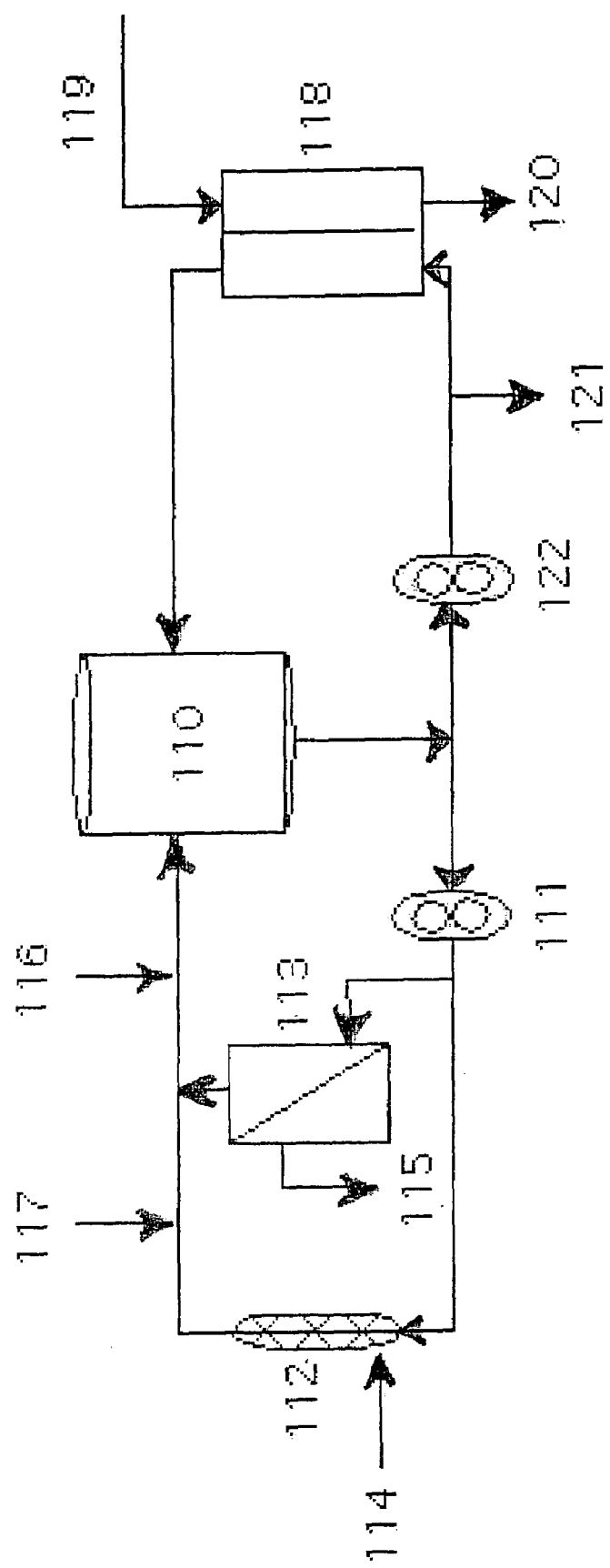
FIG. 2 is a schematic of the process for polymerizing a stabilized hemoglobin solution (HBOC-302).

The manufacture of HBOC-302 was performed HBOC-F obtained as described above. HBOC-F was collected as a dilute solution and concentrated as described above to 9–11 g/dL. HBOC-F was maintained in the deoxygenated form by the use of nitrogen purged vessels and the use of Hoechst-Celanese phase transfer membranes in which nitrogen is passed on one side of the membrane and hemoglobin solution is recirculated on the other side of the membrane. The process was carried out in HBOC-302 process loop 210. Loop 210 (FIG. 2) comprises recirculation vessel 110, pump 111, 30 kD concentration filter (Millipore, Bedford, Mass.) 113, permeate line 115, static mixer 112, ports 114, 116, and 117, deoxygenation cartridge (Hoechst-Celanese, Charlotte, N.C.) 118, inlet 119, outlet 120, recovery port 121, and pump 122.

Reactor Preparation

The manufacturing process was initiated by adding deoxygenated water for injection (WFI) to 110. The WFI was recirculated through 113 and 118. Nitrogen gas was used to sweep the deoxygenation cartridge and deoxygenate the system to less than 1% dissolved oxygen.

HBOC-F Transfer

Approximately 37 kg of hemoglobin was transferred to 110. The hemoglobin concentration was adjusted to 4.0±0.2 g/dL with WFI. The polymerization reactor was maintained in a deoxygenated state by placing a nitrogen blanket on the reactor, and the temperature is adjusted to 42±2° C. by recirculating warm water through the reactor jacket.

Polymerization

The polymerization process converted HBOC-F to polymerized hemoglobin by addition of approximately 0.63% glutaraldehyde in WFI. The glutaraldehyde solution was added at a rate of 0.58 L/min to the hemoglobin solution through 114. An inline static mixer, 112, was used to ensure rapid mixing of the glutaraldehyde and hemoglobin. Additional mixing was supplied by an agitator in 110. Glutaraldehyde addition was continued over a period of approximately 1.5 hours until the required weight per kg of hemoglobin was added (approximately 52.2 kg of activation solution was added, 1.4 kg of activation solution per kg of hemoglobin). The temperature in the reactor was maintained at 42±2° C. throughout the activation process.

Cool and Concentrate

Polymerized hemoglobin in 110 was cooled to 20±2° C. by recirculation of chilled water in the reactor jacket. The solution was concentrated to approximately 8.5 g/dl by recirculation through 118. The temperature was maintained at 20±2° C. for the remainder of the process.

Sodium Borate Diafiltration

The pH of the polymerized hemoglobin solution was raised to 10.0 or greater by diafiltration with three volumes of deoxygenated sodium borate buffer (4.58 g/L sodium borate decahydrate and 0.90 g/L sodium hydroxide in WFI) at pH 10.4–10.6. The diafiltration was performed across 113. The sodium borate buffer was added through port 116.

Sodium Borohydride Solution Addition and Incubation

Glutaraldehyde/hemoglobin bonds were stabilized with the reducing agent sodium borohydride. A sodium borohydride solution was prepared by adding sodium borohydride (9.45 g/l) to deoxygenated sodium borate buffer solution. Approximately 51 kg of sodium borohydride solution was added through port 114 to the recirculating hemoglobin solution over approximately 90 minutes. The polymerized hemoglobin solution was pumped through 118 while flushing the other side of the cartridge membrane with nitrogen to strip out and minimize levels of hydrogen gas and oxygen in the hemoglobin solution. When the borohydride addition was completed, the solution was incubated for an additional period of one hour while continuing to recirculate over 118.

Concentration and DFA Diafiltration

Following the incubation with sodium borohydride, the stabilized polymerized hemoglobin solution was concentrated across 113 to approximately 10 g/dL. After decreasing the volume, the hemoglobin solution was diafiltered with 10 volumes of Diafiltration Solution A (DFA) to reduce the pH to 7.6 to 7.9, wash out the sodium borohydride and sodium borate buffer, and equilibrate the final bulk drug HBOC-302 with physiological buffer. DFA is 6.6 g/L sodium chloride, 0.30 g/L potassium chloride, 0.20 g/L calcium chloride dihydrate, 0.44 g/L sodium hydroxide, 2.0 g/L N-acetyl-L-cysteine, 3.04 g/L sodium lactate in WFI at pH=4.9–5.1.

Hemoglobin Analysis

Samples of the polymerized hemoglobin solution, HBOC-302, prepared as described above, were taken for GPC and Co-oximeter analysis.

Surprisingly, polymerized hemoglobin produced from HBOC-F meets the specifications for molecular weight distribution for hemoglobin blood substitute for use in animals (HBOC-301), namely high molecular weight (HMW) of not more than 10% of total hemoglobin, octamer plus tetramer of between about 40% and about 55% of total hemoglobin, dimer not more than about 5% of total hemoglobin when analyzed by GPC under dissociating conditions.

Determination of Oxygen Binding Characteristics

The partial pressure of oxygen at 50% hemoglobin oxygen saturation ($P_{50}$) of the samples was tested on a Hemox analyzer and compared with starting HBOC-F material as well as with HBOC-301. Hemoglobin concentration (THb), percent oxyhemoglobin (% oxy-Hb) and percent methemoglobin (% metHb) were measured with the instrumentation laboratory co-oximeter (model IL-482, Instrumentation Laboratories, Lexington, Mass.) according to manufacturer's instructions. Percent oxyhemoglobin saturation was also measured at 20% $O_2$ levels. The THb, % oxy-Hb, and % metHb were measured in deoxygenated samples. Approximately 10 ml aliquots of each sample were transferred into a 60 cc syringe. Samples were oxygenated with air for at least 15 minutes on a slow speed rotor. An aliquot of each air-oxygenated sample was tested on a co-oximeter. The remaining samples were further oxygenated using 50% $O_2$ for at least 15 minutes and retested on the co-oximeter.

No significant differences in oxygen binding characteristics were seen between HBOC-302, HBOC-F, HBOC-301 and HBOC-201 in the gas equilibration study. Surprisingly, the polymerized stabilized hemoglobin samples (HBOC-302) have similar equilibrium oxygen binding characteristics compared to HBOC-301 and compared to the starting material, HBOC-F. At 20% $O_2$, all samples were about 90% to about 96% saturated. At 50% $O_2$, all samples were about 98% to about 100% saturated.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for forming a polymerized hemoglobin solution from a stabilized hemoglobin solution, wherein, the stabilized hemoglobin solution includes hemoglobin that has previously been exposed to glutaraldehyde and then subsequently to a reducing agent, comprising the step of:
exposing the stabilized hemoglobin solution to glutaraldehyde to further polymerize at least a portion of the hemoglobin present in the stabilized hemoglobin solution, whereby the average molecular weight of the stabilized hemoglobin solution increases to thereby produce the polymerized hemoglobin solution.

2. A method of claim 1, wherein the stabilized hemoglobin is present in a physiological buffer when contacted with glutaraldehyde.

3. A method of claim 2, wherein the physiological buffer has a pH of about 7.6 to about 7.9.

4. A method of claim 2, wherein the physiological buffer includes at least one component selected from the group consisting of: sodium lactate, N-acetyl-L-cysteine, sodium chloride, potassium chloride, and calcium chloride.$2H_2O$.

5. A method of claim 3, wherein the physiological buffer includes sodium lactate at a concentration of about 290 to about 330 mg/100 ml.

6. A method of claim 3, wherein the physiological buffer includes N-acetyl-L-cysteine at a concentration of about 130 to about 220 mg/100 ml.

7. A method of claim 3, wherein the physiological buffer includes sodium chloride at a concentration of about 570 to about 620 mg/100 ml.

8. A method of claim 3, wherein the physiological buffer includes potassium chloride at a concentration of about 27 to about 33 mg/100 ml.

9. A method of claim 3, wherein the physiological buffer includes calcium chloride.$2H_2O$ at a concentration of about 18 to about 22 mg/100 ml.

10. A method of claim 1, wherein the stabilized hemoglobin solution comprises bovine hemoglobin.

11. A method of claim 1, wherein the concentration of the hemoglobin in the stabilized hemoglobin solution during the further polymerization is about 40 grams per liter.

12. A method of claim 1, wherein the concentration of glutaraldehyde added to the stabilized hemoglobin solution is about 1 to about 20 grams of glutaraldehyde per kilogram of total hemoglobin present in the stabilized hemoglobin solution.

13. A method of claim 12, wherein the concentration of glutaraldehyde in the stabilized hemoglobin solution is about 10 grams of glutaraldehyde per kilogram of total hemoglobin present in the stabilized hemoglobin solution.

14. The method of claim 1, wherein no more than about 10% by weight of the hemoglobin present in the polymerized hemoglobin solution has a molecular weight of at least about 500 kD.

15. A method of claim 1, wherein between about 45% and about 65% by weight of total hemoglobin present in the polymerized hemoglobin solution is tetrameric and octameric hemoglobin.

16. A method of claim 1, wherein no more than about 40% by weight of total hemoglobin present in the polymerized hemoglobin solution has as molecular weight of about 65 kD or less.

17. A method of claim 1, wherein no more than 10% by weight of total hemoglobin present in the polymerized hemoglobin solution is methemoglobin.

18. The method of claim 1, further comprising directing the polymerized hemoglobin through a filter having a molecular weight cut off of at least about 100 kD, whereby the resulting retentate comprises a polymerized hemoglobin, wherein no more than about 15% by weight of the hemoglobin present in the retentate has a molecular weight of at least about 500 kD, and no more than about 10% by weight of the hemoglobin present in the retentate has a molecular weight of about 65 kD or less.

19. A method for forming a polymerized hemoglobin solution from a stabilized hemoglobin solution, wherein the stabilized hemoglobin solution includes hemoglobin that has previously been exposed to glutaraldehyde, and then subsequently to a reducing agent and a physiological buffer, comprising the step of:

exposing the stabilized hemoglobin solution to glutaraldehyde at a concentration of about 1 to about 20 grams of glutaraldehyde per kilogram of hemoglobin present in the stabilized hemoglobin solution to further polymerize at least a portion of the hemoglobin present in the stabilized hemoglobin solution, whereby the average molecular weight of the stabilized hemoglobin solution increases to thereby produce the polymerized hemoglobin solution.

20. A method of claim 19, wherein the physiological buffer has a pH of about 7.6 to about 7.9.

21. A method of claim 19, wherein the physiological buffer includes at least one component selected from the group consisting of: sodium lactate, N-acetyl-L-cysteine, sodium chloride, potassium chloride, and calcium chloride.2H$_2$O.

22. A method of claim 19, wherein the physiological buffer includes sodium lactate at a concentration of about 290 to about 330 mg/100 ml.

23. A method of claim 19, wherein the physiological buffer includes N-acetyl-L-cysteine at a concentration of about 130 to about 220 mg/100 ml.

24. A method of claim 19, wherein the physiological buffer includes sodium chloride at a concentration of about 570 to about 620 mg/100 ml.

25. A method of claim 19, wherein the physiological buffer includes potassium chloride at a concentration of about 27 to about 33 mg/100 ml.

26. A method of claim 19, wherein the physiological buffer includes calcium chloride.2H$_2$O at a concentration of about 18 to about 22 mg/100 ml.

27. A method of claim 19, wherein the stabilized hemoglobin solution comprises bovine hemoglobin.

28. A method of claim 19, wherein the concentration of the hemoglobin in the stabilized hemoglobin solution during the further polymerization is about 40 grams per liter.

29. The method of claim 19, further includes the step of forming the stabilized hemoglobin solution.

30. A method of claim 19, wherein the concentration of glutaraldehyde added to the stabilized hemoglobin solution is about 10 grams of glutaraldehyde per kilogram of total hemoglobin present in the stabilized hemoglobin solution.

31. A method of claim 19, wherein no more than about 10% by weight of the hemoglobin present in the polymerized hemoglobin solution has a molecular weight of greater than about 500 kD.

32. A method of claim 19, wherein between about 45% and about 65% by weight of total hemoglobin present in the polymerized hemoglobin solution is tetrameric and octameric hemoglobin.

33. A method of claim 19, wherein no more than about 40% by weight of total hemoglobin present in the polymerized hemoglobin solution has a molecular weight of about 65 kDa or less.

34. The method of claim 19, wherein the stabilized hemoglobin has a pH of about 7.6 to about 7.9, and is a component of a solution that includes a) N-acetyl-L-cysteine at a concentration of about 130 to about 220 mg/100 ml b) sodium lactate at a concentration of about 290 to about 330 mg/100 ml:

c) sodium chloride at a concentration of about 570 to about 620 mg/100 ml:

d) potassium chloride at a concentration of about 18 to about 22 mg/100 ml; and e) calcium chloride.2H$_2$O at a concentration of about 18 to about 22 mg/100 ml, and wherein the polymerized hemoglobin solution includes no more than about 10% by weight of total hemoglobin present in the hemoglobin solution has a molecular weight of at least about 500 kDa, no more than about 40% by weight of total hemoglobin has a molecular weight of about 65 kD or less, and no more than about 10% by weight of total hemoglobin is methemoglobin.

35. A method of claim 34, wherein the stabilized hemoglobin solution comprises bovine hemoglobin.

36. A method of claim 34, wherein the concentration of the hemoglobin in the stabilized hemoglobin solution during the further polymerization is about 40 grams per liter.

37. The method of claim 34, further including the step of directing the stabilized hemoglobin solution through a filter having a molecular weight cut off of at least about 100 kD, to thereby form a retentate of the polymerized hemoglobin solution, wherein no more than about 15% by weight of the hemoglobin present in the retentate has a molecular weight of at least about 500 kD, and no more than about 10% by weight of the hemoglobin present in the retentate has a molecular weight of about 65 kD or less.

38. A method for forming a polymerized hemoglobin solution from a stabilized hemoglobin solution, comprising the steps of:

a) exposing a solution containing native hemoglobin to glutaraldhyde to form a hemoglobin solution containing polymerized hemoglobin;

b) exposing the hemoglobin solution that contains polymerized hemoglobin to a reducing agent to form a stabilized hemoglobin solution; and c) further exposing the stabilized hemoglobin solution to glutaraldehyde to further polymerize at least a portion of the hemoglobin present in the stabilized hemoglobin solution, whereby the average molecular weight of the stabilized hemoglobin solution increases to thereby produce the polymerized hemoglobin solution.

39. The method of claim 38, further including the step of adding sodium borohydride to the further polymerized hemoglobin solution to thereby form said polymerized hemoglobin solution.

40. The method of claim 38, wherein the reducing agent is sodium borohydride.

41. The method of claim 1, further including the step of adding sodium borohydride to the further polymerized hemoglobin solution to thereby form said polymerized hemoglobin solution.

* * * * *